United States Patent [19]

Glucksman et al.

[11] Patent Number: 4,731,520

[45] Date of Patent: Mar. 15, 1988

[54] AROMA DIFFUSER APPARATUS

[75] Inventors: Dov Z. Glucksman, Winchester, Mass.; Eugene Puchalski, Jr., Jersey City; Mark E. Hardy, Eatontown, both of N.J.

[73] Assignee: Charles of the Ritz Group Ltd., New York, N.Y.

[21] Appl. No.: 878,096

[22] Filed: Jun. 24, 1986

[51] Int. Cl.⁴ .............................................. A61L 9/03
[52] U.S. Cl. ................................... 219/271; 219/275; 219/276
[58] Field of Search ............... 219/271, 272, 273, 274, 219/275, 276, 502; 239/135, 136, 44, 46, 47, 51, 51.5, 53, 54, 55, 56, 57, 58, 59, 60; 422/305, 306, 125; 43/129

[56] References Cited

U.S. PATENT DOCUMENTS

| | | | |
|---|---|---|---|
| 2,513,919 | 7/1950 | Costello | 219/272 |
| 2,562,960 | 8/1951 | Stern | 422/305 |
| 2,611,068 | 9/1952 | Wellens | 219/272 |
| 2,756,322 | 7/1956 | Sibert | 219/275 |
| 2,931,880 | 4/1960 | Yaffe | 219/271 |
| 2,942,090 | 6/1960 | Diehl | 219/271 |
| 3,080,624 | 3/1963 | Weber, III | 422/125 |
| 3,352,490 | 11/1967 | Dalzell | 219/502 |
| 3,895,928 | 7/1975 | Moran | 219/271 |
| 3,972,473 | 8/1976 | Harrison | 239/34 |
| 4,003,967 | 1/1977 | Potvin | 219/276 |
| 4,084,732 | 4/1978 | Dearling | 222/402.17 |
| 4,214,146 | 7/1980 | Schimanski | 219/274 |
| 4,346,059 | 8/1982 | Spector | 422/125 |
| 4,571,485 | 2/1986 | Spector | 219/276 |

OTHER PUBLICATIONS

Aroma Disc Player, USC and Care Manual, 1984.

Primary Examiner—E. A. Goldberg
Assistant Examiner—Teresa J. Walberg
Attorney, Agent, or Firm—Lerner, David, Littenberg, Krumholz & Mentlik

[57] ABSTRACT

An aroma diffuser assembly for dispensing an aroma from a replaceable and expendable cartridge is provided. The cartridge includes a porous block for holding a relatively large quantity of aroma producing liquid and a protective cartridge housing for covering the block to allow handling of the cartridge without coming in contact with the block. The assembly includes a diffusion housing containing a heater assembly and blades for coupling the heater assembly to an electrical outlet. The diffuser housing is adapted to receive the cartridge and support it above the heater assembly. The cartridge housing and block have slots and channels aligned with a slot in the diffusion housing to allow heated air to impinge on the block to vaporize the liquid and to pass freely into the ambient atmosphere. Should condensation of the vapor occur on the interior walls of the cartridge, the condensed liquid is collected by troughs at the bottom of the cartridge. The block includes projecting portions which engage the channel formed by the troughs to reabsorb the liquid.

26 Claims, 6 Drawing Figures

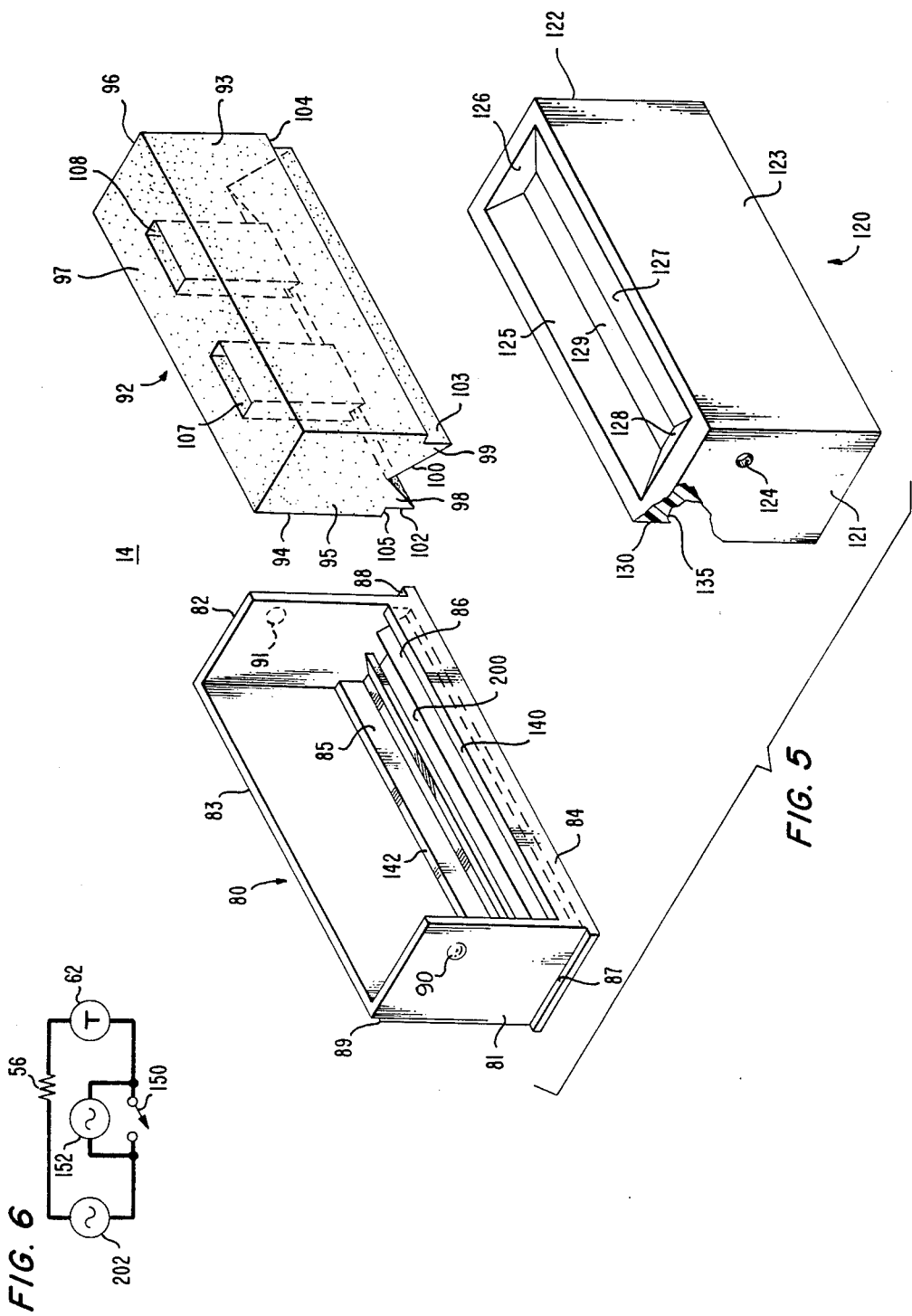

4,731,520

AROMA DIFFUSER APPARATUS

BACKGROUND OF THE INVENTION

The present invention relates to an aroma diffuser assembly and more particularly to a replaceable cartridge for the aroma diffuser assembly for long term use.

An example of a deodorizer using an electrical heating element to disseminate aroma producing vapors is disclosed in U.S. Pat. No. 2,942,090 issued to C. C. Diehl. In Diehl, a housing containing a light bulb is adapted to be connected to a conventional wall plug receptacle. The housing includes means for supporting a number of deodorant disseminating tablets within the housing. The heat from the light bulb causes an air flow past the tablets thereby imparting an aroma to the air. When the tablets are exhausted they can be replaced by removing the deodorizer from the outlet.

Alternative methods of generating aromas use aroma producing liquids sprayed or placed on an absorbent pad located above a heat source such as a light bulb. The liquid volatizes more quickly providing an instant aroma to the air when the unit is turned on. Heated air passes through the pad producing an aroma as it moves into the ambient atmosphere. See U.S. Pat. No. 4,346,059 issued to Donald Spector. The liquid is confined within a bottle and is sprayed onto the pad when required in a controlled fashion. See also U.S. Pat. No. 4,556,539 issued to Donald Spector for a disc playing aroma generator which uses a disc formed of a circular sheet of absorbent material impregnated with a liquid fragrance and sandwiched between a pair of annular plastic films which are peripherally joined to create a central zone exposing the impregnated sheet. The disc is quite thin and the volume of liquid fragrance to be dispensed is limited by the disc shape.

Many other examples of aroma generating devices exist. It is desirable, however, to provide an aroma diffuser and replaceable cartridge therefore which is easy to use, uses aroma-producing liquids to provide the aroma but which avoids the complexity of handling such liquids to avoid the messiness associated therewith, and which provides a large quantity of aroma producing liquid to be dispensed for long term use.

SUMMARY OF THE INVENTION

An aroma diffuser assembly having a diffuser housing and an aroma cartridge containing aroma producing liquid is provided. The diffuser housing has a back wall with side walls and a louvered front wall. The assembly further comprises a heater assembly attached to the housing spaced apart from the back and front walls. A ledge attached to the back and front walls above the heater assembly is provided as a support for the cartridge assembly. The ledge has a slot or opening to allow heated air to pass through and impinge on the cartridge. The back and side walls extend upwardly beyond the ledge to partially confine the cartridge.

In the preferred embodiment, the heater assembly comprises a flat plate attached to a post extending away from the back wall to position the flat plate in a plane substantially parallel with the front and back walls. The heater assembly further includes a rope element which is wrapped around the plate horizontally. Means are provided for coupling and decoupling the heater element to a power source including means responsive to light and parallel manual switching means.

The cartridge assembly comprises a porous aroma block for holding a quantity of an aroma producing liquid and a housing for holding the block. The cartridge housing includes a base for supporting the cartridge assembly in the diffuser assembly housing and a wall portion extending upwardly from the base to surround the block.

The cartridge housing further includes a trough adjacent the wall portion where the wall portion meets the base. The trough collects liquid from the block due to vapors condensing on the cartridge housing walls. The block has a projecting portion which engages the trough to reabsorb the condensed liquid into the block. In the preferred embodiment the cartridge housing and block include a pair of spaced apart end walls and a pair of spaced apart side walls and include a pair of troughs adjacent and in engagement with the larger cartridge housing side walls. The block includes a pair of spaced apart triangularly shaped projections adapted for engagement with the troughs.

The cartridge housing includes a top surface for covering the block, the top surface containing a longitudinal slot. The block has at least one channel, open at both ends which extends from the bottom of the block from between the longitudinal projection to the top of block directly beneath the slot in the top surface. In the preferred embodiment, the cartridge housing includes a cradle having a pair of spaced apart end walls connected together by a side wall. The side walls and end wall extend upwardly from the base. A cradle cover with two end walls, a side wall and slotted top surface is adapted to snap together with the cradle to surround the block. Means are provided for locking the cradle and cradle cover together.

BRIEF DESCRIPTION OF THE INVENTION

FIG. 5 is an exploded view of the cartridge assembly portion of the aroma diffuser assembly.

FIG. 6 is a block diagram schematic of an electrical circuit portion of the diffuser assembly of FIGS. 1 through 5.

DETAILED DESCRIPTION OF THE INVENTION

Figure 2:
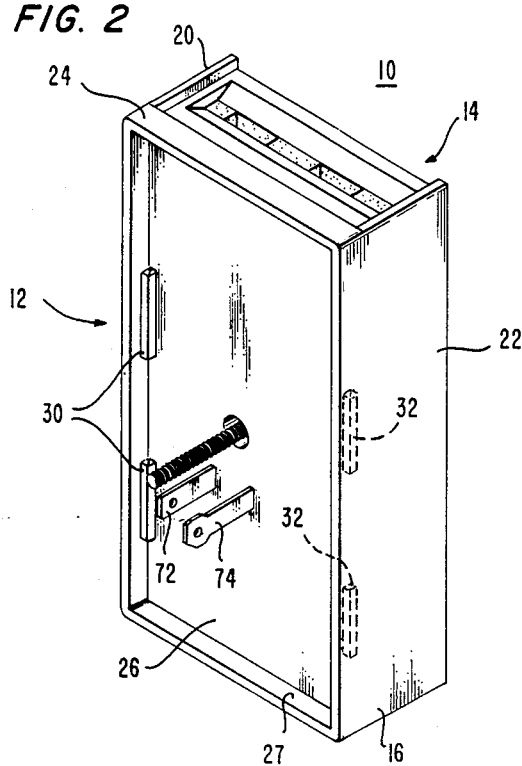
FIG. 2 is a back perspective view of an aroma diffuser assembly of FIG. 1.
Figure 1:
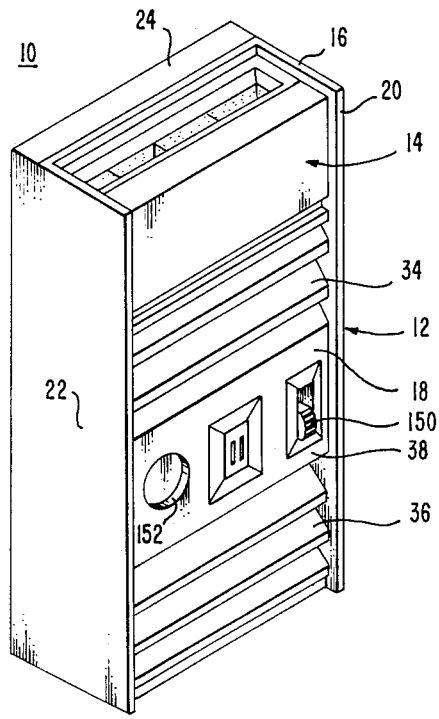
FIG. 1 is a front perspective view of an aroma diffuser assembly embodying the present invention.

Referring now to the figures, an aroma diffuser assembly designated generally 10 embodying the present invention comprises a housing 12 which supports an aroma dispensing cartridge designated generally 14. The housing 12 may be molded of suitable plastic material and in the preferred embodiment comprises a back plate 16 and a front cover 18.

The back plate comprises opposite side walls 20 and 22 connected by back side 26. The side walls extend past the back side 26 a short distance and the side walls are connected together at their top and bottom along the short distance by edges 24 and 27, respectively, all of which creates a recessed area in the back of the diffuser assembly. The back side 26 contains two pairs of slots adjacent the meeting of the back side 26 with the side walls 20 and 22, respectively. In the preferred embodiment, the back plate including the back side 26, side walls 20 and 22 and the edges 24 and 27 are integrally formed as one piece.

The front cover comprises a front surface with a first horizontally louvered area 34 spaced apart from a second horizontally louvered area 36 by a flat surface 38. Each side edge of the front cover has a pair of tabs 30 and 32, respectively, which extend away from the front surface substantially perpendicular thereto. The tabs are adapted to snap into the pairs of slots in the back side 26 to attach the front cover to the back plate. The front surface of the front cover is integrally formed with a bottom surface 40 which extends perpendicularly away from the front surface in the same direction as the tabs.

When the two piece housing is snapped together it forms an interior compartment 42 formed by the front cover with front louvered surfaces 34 and 36, the bottom surface 40, and the side walls 20 and 22 and back side 26 of the back plate 16. At the top the compartment is formed by ledges 44 and 46. Ledge 44 is integrally formed with back side 26 and extends perpendicularly away therefrom toward the front cover. It is positioned below the edge 24 and is even with a horizontal ledge 46 at the top of front cover 18. The ledge 44 and ledge 46 are spaced apart from one another to form a slot 48. The interior of compartment 42 communicates with ambient atmosphere through the louvered surfaces 34 and 36 on the front cover 18 and through the slot 48.

The aroma diffuser assembly further comprises a heater assembly designated generally 50 which comprises a metallic mounting plate 52 with a mounting hole 54, a 720 ohm rope heater element 56 wrapped around the mounting plate 52 and two wire leads for connecting the terminals of the heater element to a power source such as an AC outlet. A thermostat 62 and thermo fuse 64 are coupled in series between one end of the rope element 56 and one of the wire leads. The back plate 16 comprises a post 68 integrally formed therewith and extending away from the back side 26 into the compartment 42. The heater assembly 50 is mounted to the back plate by inserting the post 68 through the mounting hole 54 in the plate and securing it thereto with star washer 70 shown in FIG. 5.

The wire leads are coupled to a pair of electrical outlet receptacle blades 72 and 74 which are mounted to the back plate 16 and which pass through slots in the back plate as shown in FIG. 2; hence, the entire aroma diffuser assembly 10 is adapted for connection to an electrical outlet.

Figure 4:
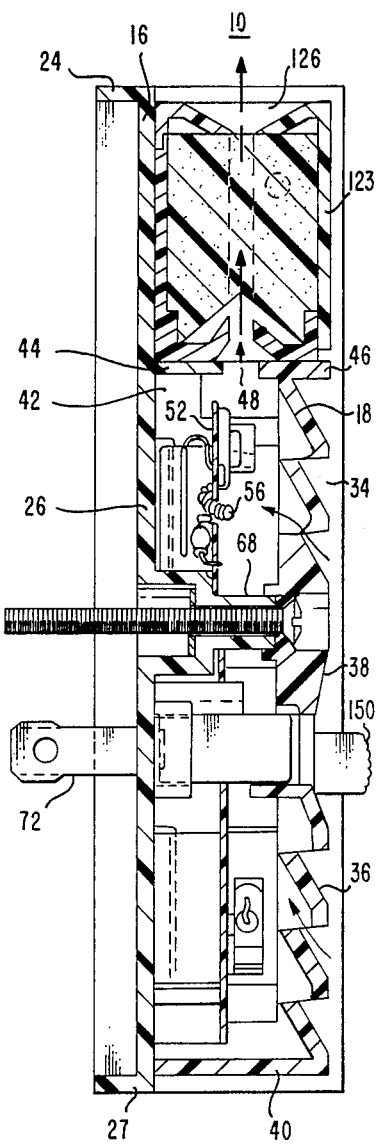
FIG. 4 is a side cross sectional view taken along the lines and arrows 4—4 in FIG. 3.
Figure 3:
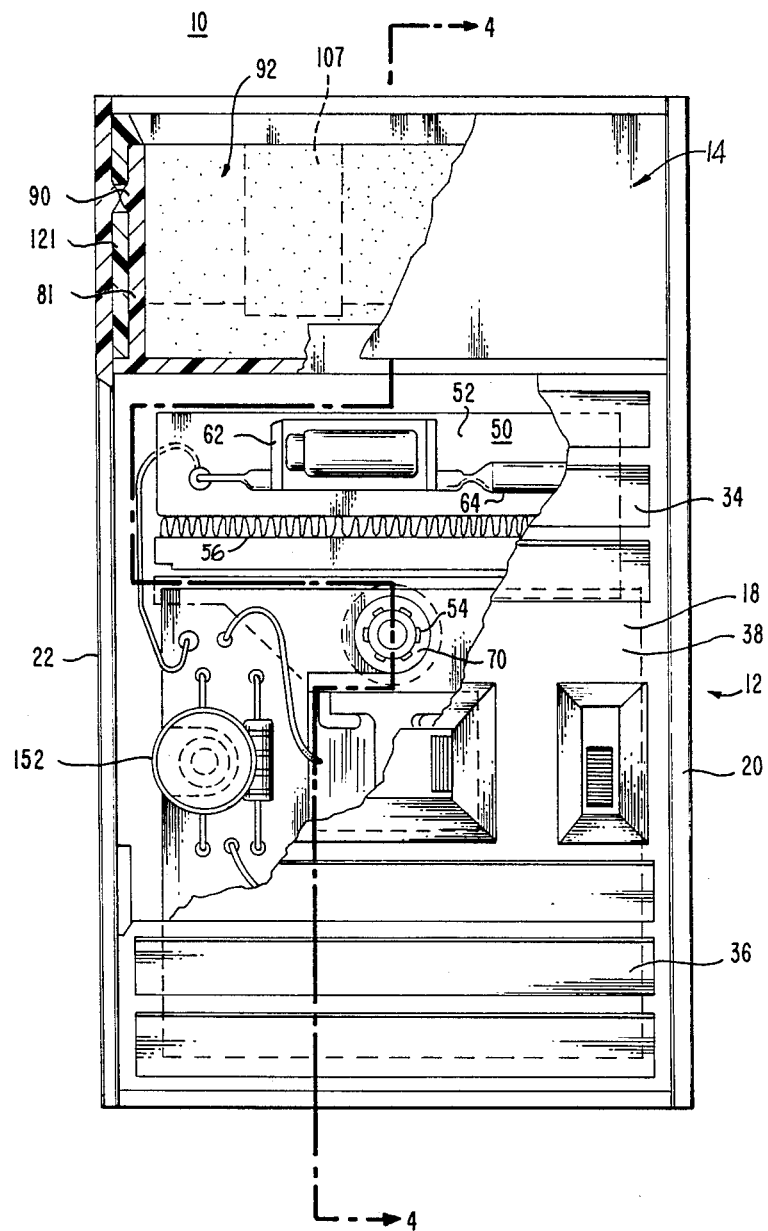
FIG. 3 is a front elevational view of the aroma diffuser assembly of FIG. 1 partially in cross section with the front shown partially broken away.

Referring now to FIG. 4, details of the cartridge assembly 14 are shown in more detail. The cartridge assembly 14 comprises a cradle designated generally 80, an aroma block designated generally 92 and a cradle cover designated generally 120. The cradle is made of a suitable polymer such as polypropylene which is immune to attack from the various fragrances, etc. some of which are oil based and are to be diffused by the assembly 10. It comprises spaced apart side walls 81 and 82 connected together by back wall 83. The front is open. The sides and back walls are integrally formed with a rectangular base 84 and extend upwardly therefrom. A pair of parallel and spaced apart troughs 85 and 86 extend across the base 84 from one side wall 81 to the other 82. Trough 85 is adjacent to and engages the back wall 83 where it meets the base 84 while trough 86 runs along the front edge of base 84. The troughs are separated from one another forming a slot 200 in between in the bottom of the cradle. The base 84 extends outwardly from the side walls 81 and 82 to form side ledges 87 and 88 while the back wall 83 is reduced in thickness slightly at its top edge to form a ledge 89. Each side wall further comprises a bump 90 and 91 which protrude outwardly therefrom.

Aroma block 92 is preferably made of a porous plastic or polymer such as a porous polyethylene foam which is adapted to be impregnated with an oil base fragrance or other aroma producing chemical. The block is mostly rectangular in cross section with side walls 93 and 94, end walls 95 and 96 and top surface 97. The bottom of the block comprises a pair of parallel triangularly shaped protrusions 98 and 99 which run lengthwise along the block from end wall 95 to end wall 96. Where the sides of protrusions 98 and 99 meet they form an inverted V-shaped groove 100 extending inwardly into the bottom of the block. Sides 102 and 103 of protrusions 98 and 99 join the block 92 inwardly from the side walls 93 and 94 of the block to form a pair of spaced apart and parallel longitudinal ledges 104 and 105.

The aroma block 92 further comprises a pair of rectangularly shaped channels 107 and 108 which extend from the apex of the inverted V-shaped groove at the bottom of the block to the top surface 97. The channels are open to ambient atmosphere at both ends and each is approximately 0.500 inches long and 0.125 inches wide. They are spaced apart from end walls 95 and 96 and lie generally along the center line between side walls 93 and 94.

The cradle cover 120 is also generally rectangular in shape and comprises a polymer such as polypropylene. It comprises end walls 121 and 122 joined by back wall 123. End walls 121 and 122 are equipped with a hole or indentation such as the hole 124 on end wall 121. The bottom is completely open as is the front opposite back wall 123. The top surface is formed with four sloping wall portions 125 through 128 which slope downwardly toward one another. They don't completely close off the top leaving a rectangular slot 129 whose largest dimension runs between end walls 121 and 122.

The sloping wall portion 125 rises up to meet a downwardly directed edge 130 which if extended would form a front wall of the cradle cover. The downwardly extending edge has a reduced thickness at tip 135 which extends downwardly below the slot 129.

To assemble the cartridge the aroma block is placed in the cradle with the triangularly shaped elongated protrusions 98 and 99 inserted in the troughs 85 and 86 with the ledges 104 and 105 of the protrusions resting on the top edges 140 and 142 of the troughs 86 and 85, respectively. Next, the cradle cover is slid into position around the block and cradle with the bottom edges of the end walls 121 and 122 resting on ledges 87 and 88 of the base. The cradle cover is snapped into place by forcing the bumps 90 and 91 on the end walls 81 and 82 of the cradle 80 to slip into holes 124 in the cradle cover 120 and forcing the tip 135 of the cover to snap over back wall 83 of the cradle. Room is made to accommodate the tip by ledge 89. The tolerances are such that the back wall 123 engages trough 86 along its length.

The cradle assembly is then placed into the recess in the top of the aroma assembly formed by the top portions of the side walls 20 and 22 and back side 26 of the aroma diffusion assembly 10 and ledges 44 and 46. The bottom of the troughs 85 and 86 at the perimeter of base 84 rests on the ledges 44 and 46 to support the cartridge assembly.

In use the aroma diffuser 10 is plugged into an ordinary 120 volt wall socket which is represented by the AC source 202 in FIG. 6. The aroma diffuser is turned on by switch 150 on the front cover, or in some models a light sensitive sensor 152 also found on the front cover and parallel with the switch 150 automatically turns on the aroma dispenser when the light in the room is turned on or at the presence of daylight. The rope heater 56 then heats up the ambient air within compartment 42. The heated air rises through slot 48, through slot 200 between troughs 85 and 86 where it is funneled by the V-shaped groove 100 into the channels 107 and 108 in the aroma block 92. Air is drawn into the compartment 42 through the louvered regions 34 and 36.

The aroma block should be made from a suitable material with good porosity which will absorb a good quantity of the aroma producing liquid and which will allow the liquid to vaporize as heated air passes through. In the preferred embodiment, the block is a porous, open cell polyethylene but open cell polymers or fibrous materials would also be suitable. The aroma producing liquid is either an essential fragrance oil, either single or in combination, or a chemical. The block can be impregnated in a variety of ways, e.g., by passing it through a solution or pressing the oil into the block under pressure. In the preferred embodiment a block when filled is expected to provide up to thirty hours or more of operation.

As heated air impinges upon the V-shaped groove it causes the aroma producing liquid in the block to vaporize. The V-shaped groove helps to funnel the heated air and vapors into the chimney like channels 107 and 108 where the heated air and vapors rise through the block 92 where further vaporization of the aroma-producing liquid occurs. The chimney like openings are located directly beneath the slot 129 in the cradle cover so the heated air with aroma vapors passes therethrough into the open atmosphere. Only a slot is provided above the block since it is desirable to encapsulate the block as much as possible to avoid contact with hands or clothing by the liquid. But the aroma producing vapors in the heated air will condense against the surface of any enclosures causing dripping of the liquid down into the diffuser and possibly out the bottom of the diffuser onto the floor or rug etc. This is unsightly and undesirable.

The tolerances between the sizes of the block, cradle and cradle cover are made very close and the chimney channels are located just beneath the slot 129. This reduces the amount of vapor which will find its way between the block and the walls of the cradle and cover. Vapor which does condense on the interior walls of the cradle and cover, will run down and collect in the troughs 85 and 86 where it will be reabsorbed into the block through the triangularly shaped projections 98 and 99.

What is claimed is:

1. An aroma cartridge for an aroma diffuser comprising:
    a porous aroma block for holding a quantity of an aroma producing liquid;
    a cartridge housing for holding said aroma block, said cartridge housing having a base for supporting said cartridge on said aroma diffuser and a wall portion extending upwardly from said base to surround said block, said base having an opening therein; and
    a trough adjacent said wall portion where said wall portion meets said base, said trough disposed to collect said liquid which may condense on the interior surface of said wall portion, said block comprising a projecting portion which engages said trough to reabsorb said condensed liquid into said block.

2. The cartridge of claim 1 wherein said cartridge comprises a top surface which joins with said wall portion to cover said block, said top surface having an opening therein spaced apart from said wall portion.

3. The cartridge of claim 2 wherein said block comprises at least one channel which extends from the bottom of said block to the top of said block and open at both ends, said channel positioned directly beneath said opening in said top surface of said cartridge.

4. The cartridge housing of claim 1 wherein said wall portion comprises:
    parallel and spaced apart end walls and parallel and spaced apart side walls; and
    a pair of parallel and spaced apart troughs adjacent to and engaging said side walls.

5. The cartridge of claim 4 wherein said block comprises:
    a block having a bottom, said bottom including a pair of parallel and spaced apart longitudinal projections integrally formed with the bottom of said block and adapted to be received within said troughs.

6. The cartridge of claim 4 wherein said cartridge housing comprises:
    a cradle having parallel and spaced apart end walls, a side wall connecting said end wall; and
    a cradle cover having parallel and spaced apart end walls, a side wall connecting said end walls and top surface which joins with said cradle cover end walls and side wall, said top surface having a longitudinal slot therein, said cradle cover end walls adapted to overlap said end walls of said cradle with said side wall parallel and spaced apart from said side wall of said cradle.

7. The cartridge of claim 6 wherein said cartridge comprises means for locking said cradle cover and said cradle together about said block.

8. The cartridge of claim 4 wherein said housing comprises:
    a top surface which meets said side walls and end walls and which comprises a longitudinal slot parallel with and spaced apart from said side walls; and
    said block comprises at least one channel open at both ends extending from the bottom of said block to the top of said block, said channel located directly beneath said longitudinal slot.

9. The cartridge of claim 8 wherein said block comprises a pair of rectangularly shaped channels.

10. The cartridge of claim 9 wherein said block comprises a block having a pair of parallel and spaced apart triangularly shaped projections which form a longitudinal V-shaped groove in the center of said block which intersects said pair of channels.

11. An aroma diffuser assembly comprising:
    a removable aroma producing means for containing an aroma producing liquid for multiple hour use; and
    an aroma diffuser housing containing a heater assembly and coupling means for coupling said heater assembly to a power source;
    said housing comprising spaced apart side walls, a back wall and a front wall spaced apart from said back wall, said heater assembly positioned intermediate said front and back walls, and a ledge for supporting said aroma producing means above said heater assembly, said ledge having a slot therein to allow heated air from said heater assembly to pass through said ledge to impinge upon said aroma producing means, the side walls and back wall of said housing extending upwardly past said ledge to partially confine said aroma producing means;

said heater assembly comprising a flat plate, and a rope heating element wrapped horizontally around said plate, said plate attached to a post extending from the back wall of said housing, said plate positioned in a plane substantially parallel with said front and back walls.

12. The aroma diffuser of claim 11 wherein said coupling means comprises a pair of electrically conducting blades mounted to said diffuser housing and extending through the back wall thereof, said blades electrically coupled to said heater assembly, said pair of blades adapted to engage a standard AC electrical receptacle.

13. The diffuser assembly of claim 11 wherein said coupling means comprises:
automatic means attached to the outside of said front wall for automatically coupling and decoupling said power source to said heater element in the presence or absence of light, respectively.

14. The diffuser assembly of claim 13 wherein said coupling means comprises a manual switch attached to the outside of said front wall in parallel with said automatic means.

15. The diffuser assembly of claim 11 wherein said aroma producing means comprises a cartridge including:
a porous aroma block for holding a quantity of an aroma producing liquid;
a cartridge housing for holding said aroma block, said cartridge housing having a base for supporting said cartridge on said aroma diffuser and a wall portion extending upwardly from said base to surround said block, said base having an opening therein; and
a trough adjacent said wall portion where said wall portion meets base, said trough disposed to collect said liquid which may condense on the interior surface of said wall portion, said block comprising a projecting portion which engages said trough to reabsorb said condensed liquid into said block.

16. The cartridge housing of claim 15 wherein said wall portion comprises:
parallel and spaced apart end walls and parallel and spaced apart side walls; and
a pair of parallel and spaced apart troughs adjacent to and engaging said side walls.

17. The cartridge of claim 16 wherein said block comprises:
a block having a pair of parallel and spaced apart longitudinal projections integrally formed with the bottom of said block and adapted to engage the channels formed by said troughs.

18. The cartridge of claim 16 wherein said housing comprises:
a top surface which meets said side walls and end walls and which comprises a longitudinal slot parallel with and spaced apart from said side walls; and
said block comprises at least one channel open at both ends extending from the bottom of said block to the top of said block, said channel located directly beneath longitudinal slot.

19. The cartridge of claim 18 wherein said block comprises a pair of rectangularly shaped channels.

20. The cartridge of claim 19 wherein said block comprises a block having a pair of parallel and spaced apart triangularly shaped projections which form a longitudinal V-shaped groove in the center of said block which intersects said pair of channels.

21. The cartridge of claim 16 wherein said cartridge housing comprises:
a cradle having parallel and spaced apart end walls, a side wall connecting said end wall; and
a cradle cover having parallel and spaced apart end walls, a side wall connecting said end walls and top surface which joins with said cradle cover end walls and side wall, said top surface having a longitudinal slot therein, said cradle cover end walls adapted to overlap said end walls of said cradle with aid side wall parallel and spaced apart from said side wall of said cradle.

22. The cartridge of claim 21 wherein said cartridge comprises means for locking said cradle cover and said cradle together about said block.

23. The cartridge of claim 15 wherein said cartridge comprises a top surface which joins with said wall portion to cover said block, said top surface having an opening therein spaced apart from said wall portion.

24. The cartridge of claim 23 wherein said block comprises at least one channel which extends from the bottom of said block to the top of said block and open at both ends, said channel positioned directly beneath said opening in, said top surface of said cartridge.

25. An aroma diffuser assembly comprising:
a removable aroma producing means for containing an aroma producing liquid for multiple hour use; and
an aroma diffuser housing containing a heater assembly and coupling means for coupling said heater assembly to a power source, said aroma diffuser housing adapted to support said aroma producing means above said heater assembly,
said aroma producing means comprising a cartridge including a porous aroma block for holding a quantity of an aroma producing liquid, a cartridge housing for holding said aroma block, said cartridge housing having a base for supporting said cartridge on said aroma diffuser and a wall portion extending upwardly from said base to surround said block, said base having an opening therein, and a trough adjacent said wall portion where said wall portion meets said base, said trough disposed to collect said liquid which may condense on the interior surface of said wall portion, said block including a projection portion which engages said trough to reabsorb said condensed liquid into said block.

26. An aroma diffuser assembly comprising:
a removable aroma producing means for containing an aroma producing liquid for multiple hour use; and
an aroma diffuser housing having front and back walls containing a heater assembly and coupling means for coupling said heater assembly to a power source, said aroma diffuser assembly adapted to support said aroma producing means above said heater assembly;
said heater assembly comprising a flat plate, and a rope heating element wrapped horizontally around said plate, said plate attached to a post extending from the back wall of said housing, said plate positioned in a plane substantially parallel with said front and back walls.

* * * * *

UNITED STATES PATENT AND TRADEMARK OFFICE
CERTIFICATE OF CORRECTION

PATENT NO. : 4,731,520

DATED : March 15, 1988

INVENTOR(S) : Glucksman et al.

It is certified that error appears in the above-identified patent and that said Letters Patent is hereby corrected as shown below:

Column 4, line 35, "suoh" should read --such--.
Column 7, line 19, "thrugh" should read --through--.
Column 7, line 42, after "meets" insert --said--.
Column 7, line 68, after "beneath" insert --said--.

Signed and Sealed this

Twelfth Day of July, 1988

Attest:

DONALD J. QUIGG

Attesting Officer

Commissioner of Patents and Trademarks